United States Patent
Nakata et al.

(10) Patent No.: US 9,701,937 B2
(45) Date of Patent: Jul. 11, 2017

(54) CARRIER FOR CULTIVATION OF CELLS

(75) Inventors: Ken Nakata, Suita (JP); Kanae Kasai, Tokyo (JP)

(73) Assignees: KOKEN CO., LTD., Toshima-ku, Tokyo (JP); OSAKA UNIVERSITY, Suita-shi, Osaka (JP)

( * ) Notice: Subject to any disclaimer, the term of this patent is extended or adjusted under 35 U.S.C. 154(b) by 1044 days.

(21) Appl. No.: 12/319,330

(22) Filed: Jan. 6, 2009

(65) Prior Publication Data

US 2010/0173415 A1   Jul. 8, 2010

(51) Int. Cl.
  *C12N 5/00*  (2006.01)

(52) U.S. Cl.
  CPC ........ *C12N 5/0068* (2013.01); *C12N 2533/54* (2013.01)

(58) Field of Classification Search
  CPC .......................... C12N 5/0068; C12N 2533/54
  See application file for complete search history.

(56) References Cited

U.S. PATENT DOCUMENTS

| | | | |
|---|---|---|---|
| 4,600,533 A * | 7/1986 | Chu | 530/356 |
| 5,206,028 A * | 4/1993 | Li | 424/484 |
| 5,256,418 A * | 10/1993 | Kemp et al. | 424/423 |
| 5,906,937 A * | 5/1999 | Sugiyama et al. | 435/371 |
| 2004/0134502 A1* | 7/2004 | Mizuno et al. | 128/898 |

OTHER PUBLICATIONS

Maffia et al. Collagen Processing. JALCA, vol. 99, 2004. p. 164-169.*
"Effects of Compressive Loading on Human Synovium-derived Cells" by Y. Muroi et al, J. Dent. Res. 86(8), 2007, pp. 786-791.
Collagen, by H. Itoh et al, Polymeric Materials Encyclopedia, vol. 2, 1996, pp. 1287-1290.
Collagen Fibril Formation, by B. Williams et al, The Journal of Biological Chemistry, vol. 253, No. 18, 1978, pp. 6578-6585.

* cited by examiner

*Primary Examiner* — Taeyoon Kim
(74) *Attorney, Agent, or Firm* — Flynn, Thiel, Boutell & Tanis, P.C.

(57) ABSTRACT

A carrier for cell cultivation having stress of 10-30 kPa at 10% load, preparing a material, which has physical property similar to cartilage tissue of vivo, by lyophilization using high concentrated collagen dispersion, solution or mixture thereof as a starting material, then performing insolubilizing treatment to regulate physical strength and absorption speed in a living body.

1 Claim, 1 Drawing Sheet

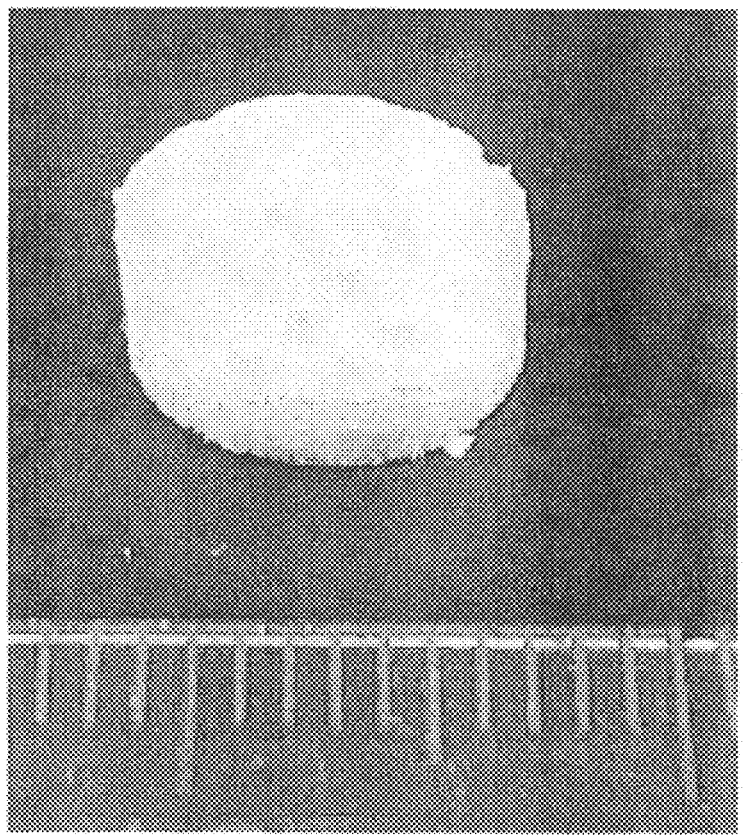

CARRIER FOR CULTIVATION OF CELLS

FIELD OF THE INVENTION

The present invention relates to a carrier for cell cultivation and more specifically relates to a carrier for cartilage cell cultivation.

DESCRIPTION OF THE PRIOR ART

Semilunar bone in knee articulation (meniscus) is a firocartilage tissue in articulation and bears with various functions such as shock absorbing, load dispersing, improvement of smooth action or stabilizing of articulation, and is easily injured during sporting or in ordinary vital action. Injury causes pain of knee articulation and restriction of motion and natural healing is difficult. Usually, to an injured semilunar bone, which cannot be healed by conservative treatment such as pharmacotherapy or kinesiatrics, an operation is performed and an ectomy of the semilunar bone or partial ectomy of semilunar bone is carried out, however, by said operation, the function of the semilunar bone is damaged. Recently, along with the improvement of endoscopic techniques, suturing of semilunar bone under the sight of arthroscope becomes possible and retain of function is being attempted.

However, injury with deficit, complicated injury or denatured scissura cannot be an object of suture and the problem that the function of semilunar bone cannot be repaired is pointed out. This problem is not limited to semilunar bone, and is a problem of whole firocartilage tissue in which transits of vessel are few.

As the method to solve the problem, regenerative therapy is heartily investigated. And in the regenerative therapy, cell, carrier and activated factor are pointed out as three essential factors, namely, carrier for cultivation is recognized as an important factor.

A carrier having the most suitable shape and physical properties to the cells to be cultured should be selected, and in the case of cultivation of cartilage, it is desirable to have physical property and shape similar to a cartilage tissue in vivo from the first stage of cultivation.

However, a conventional carrier cannot be said to have similar physical property and shape to a cartilage tissue in vivo. Accordingly, there are problems, for example, the carrier itself does not have strength similar to cartilage, it is difficult to fit with specific shape of cartilage tissue, does not produce matrix component of cartilage at cultivation process and contains material besides a living body component.

According to Patent Document 1, an equivalent subject to implantation tissue characterizing that fixation to a periphery part of tissue after implantation is performed fast, by changing density of surface part and inner part of cartilage tissue using collagen gel, is disclosed.

In Patent Document 2, prolification in collagen of cartilage cells on membrane filter in medium, is disclosed.

In Patent Document 3, a scaffedding implant for reconstruction of cartilage using a mixture of type I and II collagen as a starting material is disclosed.

In Patent Document 4, a tissue reconstruction material and implantation material which maintain three dimensional structure by combining collagen sponge and absorbable synthetic polymer is disclosed.

Patent Document 1: JP2002-233567 A Publication
Patent Document 2: JP2003-135056 A Publication
Patent Document 3: JP2003-180815 A Publication
Patent Document 4: WO2003-011353 A Publication However, in Patent Documents 1, 2 and 3, although three-dimensional cultivation being similar to a living body is possible, similar physical property to tissue of living body cannot be obtained. Further, in Patent Document 4, although a carrier having similar strength to tissue can be produced, other synthesized object besides a matrix component of living body is contained, therefore, cannot be said as the most suited implant.

OBJECT OF THE INVENTION

The object of the present invention is a cell cultivation carrier whose starting material is collagen, which is a matrix component of cartilage tissue, having similar physical property to cartilage tissue of a living body from the first stage of cultivation and having a shape of part to be implanted. Further, it is necessary that the carrier has pores in which cells can be inserted. Still further, if cultivation to which a load that a cartilage cell or cartilage tissue suffers is added becomes possible, preparation of an implantation object similar to a tissue of living body becomes possible by cultivation.

BRIEF SUMMARY OF THE INVENTION

The gist of the present invention is a cell cultivation carrier having stress of 10-30 kPa at 10% load, preparing a material, which has physical properties similar to cartilage tissue of living body, by lyophilization using high concentrated collagen dispersion, solution or mixture thereof as a starting material, then performing insolubilizing treatment to regulate physical strength and absorption speed in a living body.

INDUSTRIAL APPLICABILITY

By use of the cell cultivation carrier of the present invention, after cartilage cell is implanted to said cell cultivation carrier, said cell cultivation carrier is fused with cartilage tissue of itself, even if immediately after implantation or after cultivation. Further, after cell is implanted, cultivation adding a load that cartilage cell or cartilage tissue in a living body suffers becomes possible, and an implanted subject more similar to tissue in vivo can be obtained by cultivation.

BRIEF ILLUSTRATION OF THE DRAWING

FIG. 1 is a cross-sectional view of a carrier which is obtained in Example 1.

DESCRIPTION OF PREFERRED EMBODIMENT

The cell cultivation carrier of the present invention can be prepared using collagen as a starting material. As a collagen to be used, an insoluble collagen extracted from tissue in vivo such as tendon collagen originating from an Achilles tendon or collagen originating from skin, soluble or solubilized collagen such as enzyme solubilized collagen (atelocollagen), alkali solubilized collagen, acid soluble collagen or salt soluble collagen can be used, in particular atelocollagen is desirable. There is no limitation in animal species, and any kind of collagen which has denaturation temperature characterized that collagen does not cause heat denaturation at cultivation can be used without problem. Specifically, collagen originated from mammal such as bovine or porcine, originated from avian such as chicken or originated from fish such as tuna or tilapia can be used. Further, recombinant collagen can be used. Chemical modified product of amino acid side chain which composes collagen, specifically acylation such as acetylation, succinilation or phthalation or esterification such as methylation or ethylation can be used.

Dispersion or solution of collagen is prepared before lyophilization is performed. In case of insoluble collagen, dispersion is used and in case of soluble collagen, it is possible to prepare solution or dispersion. pH of dispersion or solution is not restricted, however, around neutral, specifically pH4-10 is desirable.

For the purpose to associate with the strength of cartilage by lyophilization, a dried product obtained by lyophilization is pressed so as to improve the density. However, in said case it becomes difficult to implant cells into inner part of a carrier, because formed pores are broken by lyophilization.

Therefore, it is necessary to make the concentration of collagen in dispersion, solution or mixture thereof of insoluble or soluble collagen, which are the starting materials for lyophilization, 30 mg/ml or more than 30 mg/ml, desirably 50 mg/ml or more than 50 mg/ml, and a carrier having similar physical properties to cartilage tissue can be obtained. In particular, in a case of using atelocollagen, desirable concentration of collagen is 70 mg/ml or more than 70 mg/ml. In a case of lower concentration, for example, in a case of less than 30 mg/ml, since physical property of a carrier largely differs from that of a cartilage in vivo, transplantation of the carrier immediately after implantation of cartilage cells to the carrier or after cultivation becomes difficult, further, after a cell is implanted, performing of cultivation to which a load that a cartilage cell or cartilage tissue suffers is added becomes difficult.

In the present invention, the above-mentioned dispersion, solution or mixture thereof having above mentioned collagen concentration can be used, however, dispersion is especially desirable. Dispersion means a state that collagen is not dissolved but dispersed or precipitated. swelled in pH condition except where collagen can be dissolved.

When pores are contained in solution or dispersion, voids are formed by the pores in lyophilized product and the formation of voids is not desirable, therefore, it is necessary to remove pores from solution or dispersion before lyophilization. The method for removal is not restricted, however, raising of temperature that causes heat denaturation of collagen is not desirable. Specifically, heating, long term ultrasonic treatment or strong ultrasonic treatment cannot be used.

For performing lyophilization, as the first step, collagen solution, dispersion or mixture thereof is prepared and is filled into a mold of desired shape and frozen. As a method to obtain desired shape, a method to form a cube and to cut the cube to a desired shape at the actual use, or a method to use a desired mold at the first step can be mentioned, and both methods can be used preferably.

As the method to use the mold of desired shape at the first step, there is no limitation, however, for example, a method to cultivate using the carrier for cultivation of this invention, then transplant the carrier for cultivation, which contains cells, to a defected part of cartilage is desirable.

Specifically, a method to prepare a mold having a shape of defected part by photo molding method based on CT or MRI data of a patient can be mentioned.

Dispersion, solution or mixture thereof of collagen is filled into a mold and lyophization process is performed, and afore-mentioned removal process of pores can be carried out before filling process or after filling process.

As a method for freezing, rapid freezing or slow freezing can be mentioned. Since there is a possibility that pore size of a dried product becomes different depending on methods for freezing, it is necessary to select a method for freezing which can form desired pore size.

A method for drying is not restricted and ordinary method for lyophilization can be used.

To a dried product after lyophilization, insolubilizing treatment is performed. By performing insolubilizing treatment, it becomes possible to improve physical intensity of the dried product, or becomes possible to adjust remaining term of the dried product in the implanted tissue.

In a case to perform insolubilizing treatment, it is necessary to perform the insolubilizing treatment uniformly to inner part of the dried product without breaking the shape of the dried product.

As a method for insolubilizing treatment, there is no limitation, however, it is desirable to complete the treatment in short term, because when the treatment is progressed using water as a solvent, the dried product has a tendency to cause swelling and maintenance of the desired shape obtained by drying becomes difficult. And, if organic solvent is used for the purpose to prevent swelling, insolubilizing treatment of inner part of the dried product does not progress smoothly and only surface part is insolubilized, therefore the use of organic solvent is not desirable.

As a method for insolubilizing treatment of the present invention, a method by which insolubilization treatment to inner part is possible, such as dry heat treatment, γ-ray irradiation, treatment by a water-soluble chemical crosslinking agent or treatment by a vaporizable chemical crosslinking agent are desirable. Further, as a specific example of a water-soluble chemical crosslinking agent, an aldehyde compound or an epoxy compound can be used, and as a specific example of a vaporizable chemical crosslinking agent, formaldehyde can be used.

Specific processes of each insolubilization treatments are different according to the method to be used. For example, in a case of dry heat treatment, after a specimen is dried up perfectly, the specimen is stood in heated atmosphere of around 120° C. for more than 30 minutes, and in a case of γ-ray irradiation, after a specimen is wetted in a state not to cause swelling, irradiation by over than 10 krad is carried out. In a case of an insolubilization treatment by a water-soluble chemical crosslinking agent, specifically by use of glutaric aldehyde, the insolubilization treatment can be accomplished by dipping a dried product in an aqueous solution containing glutaric aldehyde by 0.5% concentration, however, for the purpose of preventing swelling from the water, the insolubilization treatment by a water-soluble chemical crosslinking agent can be performed after dry heating treatment is made to the dried product.

In a case of insolubilization treatment by a vaporizable chemical crosslinking agent, a dried product and a chemical crosslinking agent such as formalin solution are contained in a sealed container, and the insolubilization treatment accomplished by vaporized formaldehyde in the sealed container.

The carrier to which cartilage cells are implanted, can be transplanted immediately or can be transplanted after cultivation. At the cultivation, it is possible to cultivate by adding similar load that a cartilage cell or cartilage tissue in vivo suffers.

Further, at the implantation of cells into inner part of pores, it is possible to implant cells alone or can be implanted after the cells are dispersed in solution of collagen that is same material to a carrier for cultivation.

EXAMPLES

The present invention will be illustrated more in detail according to Examples, however, not intending to limit the scope of claims of the present invention to Examples.

Example 1

Bovine corium-originated enzyme solubilized collagen (atelocollagen) is added to water whose pH is adjusted to 9 using NaOH. After stirred slowly for one night and swelling the collagen sufficiently, the obtained liquid is centrifuged and dispersion of the collagen is obtained. The concentration of collagen of this dispersion is measured by the burette method. Adjusting the collagen concentration in the dispersion to be 80 mg/ml. When the collagen concentration is lower than 80 mg/ml, additional centrifugation is carried out so as to make the concentration thicker, and when the concentration is higher than 80 mg/ml, add previously mentioned water of pH 9, stir slowly and adjust the concentration by changing rotating rate and rotating time of the centrifugation.

Obtained collagen dispersion is distributed in 24 well plate for cultivation (CulterPlate™24 micro plate for cell cultivation: product of Perkin Elmer). After distribution, the plate is put into an experimental vacuum vessel, and bubbles in the dispersion are removed. After that, the plate is put into a lyophilizer whose shelf is cooled down to −20° C., and the dispersion is frozen, then vacuum drying is performed. At the drying process, the shelf is not heated.

After drying process, the dried product is picked out from the plate, contained into a desiccator with a beaker filled up with formalin solution and left for one night at room temperature.

Collagen carrier that insolubilization treatment is completed is picked out and transferred to another desiccator in which formalin solution is not contained and vacuumed by an aspirator for 3 hours, thus a carrier by which cartilage cell cultivation is possible is obtained.

Cross-sectional picture of obtained carrier is shown in FIG. 1. Dotted line locating at bottom of the picture indicates scale, and distance between one graduation is 1 mm.

Physical intensity of obtained carrier is measured. Measurement is carried out by suffering compressive load to maximum 35 kPa by 100 micro meter/sec, and stress and displacement are measured.

Obtained results show that the stress is 25 kPa at 5% loaded, 22.5 kPa at 10% loaded and 33 kPa at 20% loaded.

Further, tangent modulus is measured, and results indicate that tangent modulus is 225 kPa at 5% loaded and is 160 kPa at 10% loaded.

Above-mentioned results are obtained by distribution analysis of one-way layout.

Example 2

Dispersion of collagen is prepared by same process to Example 1 except for changing collagen concentration to 100 mg/ml, and a carrier for cultivation is prepared same as to Example 1.

Example 3

A carrier for cultivation is prepared by same process to Example 1 except for changing bovine corium-originated enzyme solubilized collagen (atelocollagen) to porcine corium-originated enzyme solubilized collagen, and a carrier for cultivation is prepared same as to Example 1.

Example 4

A carrier for cultivation is prepared by same process to Example 2 except changing bovine corium-originated enzyme solubilized collagen (atelocollagen) to porcine corium-originated enzyme solubilized collagen, and a carrier for cultivation is prepared the same as Example 1.

After obtained dried product by lyophilization same as to Example 1, said dried product is further dried under a vacuum condition at 70° C. for 2 hours. Then the dried product is heated at 120° C. under atmospheric pressure for 2 hours so as to progress insolubilization by dry heating. After that, solution is prepared by adding glutaric aldehyde of 0.5 ml/100 ml concentration into water whose pH is adjusted to 9, and the dried product to which insolubilizing treatment by dry heating is made is put in, then stirred slowly at room temperature for one hour.

Obtained carrier for cultivation is washed by water sufficiently and put in into a cultivation medium and incubated.

What is claim:
1. A collagen carrier used in cartilage cell cultivation, said collagen carrier having pores on a surface and in an inner part thereof, a stress of 10-30 kPa at 10% load and is prepared by adding an atelocollagen to water to obtain a dispersion, adjusting the collagen dispersion to have a collagen concentration of 80 mg/ml, and lyophilizing the collagen dispersion with a chemical cross-linking agent.

* * * * *